United States Patent [19]

Hollinshead

[11] Patent Number: 5,747,526
[45] Date of Patent: May 5, 1998

[54] ANTI-HIV /AIDS CHEMO(C)-, IMMUNO(I)-, OR CI-THERAPY USING TUR (OR RELATED COMPOUNDS) AND/OR NVA (OR EPV)

[76] Inventor: Ariel C. Hollinshead, 3637 Van Ness St. NW., Washington, D.C. 20008-3130

[21] Appl. No.: 591,756

[22] Filed: Jan. 25, 1996

[51] Int. Cl.$^6$ .......................... A61K 31/38; A61K 39/12
[52] U.S. Cl. .......................... 514/448; 514/21; 436/512; 530/827; 530/868; 530/350; 530/413; 549/74
[58] Field of Search .......................... 530/827, 868, 530/350, 413; 514/21, 448; 436/512; 549/74

[56] References Cited

U.S. PATENT DOCUMENTS

| | | | |
|---|---|---|---|
| 5,086,165 | 2/1992 | Marshall | 530/329 |
| 5,342,922 | 8/1994 | Marshall | 530/329 |
| 5,554,728 | 9/1996 | Basava | 530/327 |
| 5,576,429 | 11/1996 | Johansson | 536/26.8 |
| 5,593,993 | 1/1997 | Morin | 514/247 |

OTHER PUBLICATIONS

Cazzola et al. "In vivo modulating effect of a calf thymus acid lysate on human T lymphocite subsets and CD4/CD8 ration in the course of different diseases" Derwent 88–07429, 1987.

Eron et al. "Randomised tial of MNrgp120 HIV–1 vaccine in symptomless HIV–1 infection" Abst. Lancet v348, pp. 1547–1551, 1996.

Bolognesi "Prospects for prevention of and early intervention against HIV" JAMA v261, pp. 3007–3013, 1989.

*Primary Examiner*—Ceila Chang
*Attorney, Agent, or Firm*—Gary M. Nath; Todd L. Juneau; Nath & Associates

[57] ABSTRACT

Herein described is an invention of the usage, design and effective procedures 1.) for selected combined methods for preparation and 2.) for coordination of sequence, dosage and administration in utilizing anti-HIV thiophenoyl urea TUR (or related drugs) chemotherapy as well as for utilizing HIV induced or augmented nonvirion antigen NVA (or early polypeptide vaccine EPV or related or derivative) immunotherapy in treatment of HIV+ and AIDS patients (and applicable to Karposi's sarcoma and to other retroviral diseases). Herein described is an invention of 3.) the usage, design and effective procedures for a combination of TUR and NVA (or similar elements) as specific active immunochemotherapy for the treatment of HIV positive and AIDS patients, which consists of a vaccine (NVA) composed of separated and concentrated early virus-induced or augmented nonvirion polypeptides which induce long-lasting cell-mediated immunity administered at the peak of effects by a synergistic antiviral drug, TUR, which causes minimal or no resistance.

9 Claims, No Drawings

ANTI-HIV /AIDS CHEMO(C)-, IMMUNO(I)-, OR CI-THERAPY USING TUR (OR RELATED COMPOUNDS) AND/OR NVA (OR EPV)

BACKGROUND OF THE INVENTION

In spite of several years of detailed investigation there has been only minor success with current anti-HIV/AIDS therapies for various reasons, including cross-resistance to protease inhibitors, problems and lack of effective clinical outcomes with gene transfer methods, problems in usage of virus or viral gene products and problems of resistance and efficacy with single or combined chemotherapies.

An abbreviated review of some of the pertinent information from other sources may be useful in understanding the way in which we considered the problem and some of the newer information from other sources may confirm our early rationale and why we chose this approach:

(1) Infection and Disease.

In the USA, CDC reported 67,306 new cases of AIDS diagnosed in 1992, up 22% from 54,778 cases diagnosed in 1991. From 1981 through 1994, 441,528 cases have been reported, and over half have died. In 1994, about 17% were women, male homosexuals 47%. Scientists associate two viruses with AIDS. These two viruses belong to a family of viruses known as lentiviruses which are known to often induce illness in animals months or years after infection. Human immunodeficiency virus(hereafter,"HIV") is cited as the main virus which causes AIDS. There are many different subtypes of HIV-1. Subtype 0 (stands for "outlier") include up to 30 different variants, seen mainly in Cameroon and nearby regions; many of the subtype 0 variants are not detected by standard USA screening tests. Certain strains appear to be more virulent. The differences may be due to mutations producing small changes in a section known as the V3 loop of the outer covering of HIV. The World Health Organization estimates 13–15 million people in the world have HIV infection, half under age 25. Various cell surface moieties are involved in HIV attachment and penetration of the cell. There is a diversity of HIV entry, in part related to the HIV phenotype. HIV and SIV (simian) molecular biology studies include work on: Structural proteins (Gag, Env), Enzymes (Pol, PR, IN, RT), Regulatory proteins (Tat, Rev, Nef) and Accessory proteins (Vip, GVpr, Vpu and Vpx). HIV infection is generally quite aggressive during the first weeks of infection, then forms a stable relationship in humans, sometimes for 8 to 10 years. HIV levels and CD4 T lymphocyte counts change slowly, and over time CD4 cells diminish in some patients while HIV increases as a progression to AIDS takes place. HIV levels are evaluated, in part, by quantitative microculture, p24 antigen and HIV-1 DNA/RNA levels or quantitation of HIV RNA using branched DNA signal amplification. Infected humans generate 1.8 billion to 2 billion CD4 cells every day. Healthy ten year HIV carriers often have highly activated CD8+ T-lymphocytes which induce apoptosis of HIV-infected cells. HIV daily production in infected individuals is between 100 million to 680 million virions per day. Three types of lymphocyte response changes precede CD4 decline: responses to recall antigens, to alloantigens (using mixed lymphocyte reaction) and to phytohemagglutinin(PHA). HIV-infected persons slowly, stepwise, become totally unresponsive, increasing the probability of developing AIDS. Recently, a report implied that CD8+ T lymphocytes may produce three polypeptides involved in control of HIV infection, but the mechanism was unknown and postulated to be either by viral suppression or by cytolytic activity.

Other workers had shown that a strong delayed hypersensitivity cellular immune response with a type 1 cytokine profile is a better protector against HIV infection than are a strong antibody response and type 2 cytokine profile. The 3-dimensional structures of interleukin-1 (a type 1 cytokine) have been partly defined. Other type-1 cytokines include IL-12 and interferon-gamma.

Autopsy studies of AIDS patients show brain damage in from 35% (early studies) to 90% of patients. An increase in dementia and neuropathy is seen in AIDS patients, particularly sensory neuropathy and lymphoma. Sometimes leukoencephalopathy, cryptococcal meningitis or toxoplasmosis occur. Part of the increase is due to adverse effects of ddI, ddC and d4T. About 25% of all AIDS patients develop eye infections with cytomegalovirus (2) Chemical and Biologic Drugs.

(a) Anti-HIV agents.

Drugs being developed or in clinical testing are mainly designed as anti-HIV agents: Drugs like 2'3'-dideoxyinosine (ddI), azidothymidine(AZT), and Stavudine(D4T) have been clinically evaluated. Combinations such as AZT and 3TC appear to be synergistic. In studies of 305 patients, it was reported that if AZT effected a quantitative lowering of viral load, that patient would benefit from AZT 90% of the time. Changes in CD4+ T-lymphocytes were predictive only 37% of the time. N-acetylcysteine (NAC) is a precursor of the antioxidant glutathione, and once absorbed converts to cysteine on path to glutathione; it is being studied to determine if it prevents the degradation of the immune system brought about by reduced glutathione levels which retard cell division. Many nucleoside analogs are under study. It has been shown that some analogs which appear to be more active have an absolute configuration corresponding to the unnatural 1-beta-L configuration of natural nucleosides. Although the 2'3' dideoxy-nucleosides have demonstrated some clinical benefits, certain L-nucleosides like FTC, 3TC and L-FDDC have shown selective effects against HIV- as well as HBV-infected cells and are in early clinical trial. Acyclic phosphonymethylether nucleosides (PMEA), a retrovirus inhibitor, is in clinical trial with AIDS patients, and a pro-drug of PMEA, Bis(POM)PMEA designed to give orally, is in early clinical trial; the diphosphate forms act as competitive inhibitors of viral polymerases. It was found that a benzimidazole riboside BDCRB (2-bromo-5,6-dichloro-1-beta D ribofuranosyl benzimidazole) affects herpesvirus concatamer unit length mediated through a putative DNA processing enzyme chemically similar to the gene 17 bacteriophage T4 terminase. BDCRB may be useful in studies to test the prevention of one more of the three types of Karposi's sarcoma (Ks), including AIDS related sarcoma, if work using representational difference analysis identifying DNA sequences of what appears to be a new herpesvirus, in 25 of 27 samples of Ks tissues from AIDS patients, turns out to be significant. Thiopurine based oligonucleotides are reported to be potent inhibitors of HIV, cytomegalovirus and EBV replication in cell cultures at low concentrations, and are fairly nontoxic in animal studies. Pre-clinical studies of a synergistic combination of ddI with hydroxyurea, a drug which blocks cellular ribonucleotide reductase, thereby inhibiting deoxynucleotide synthesis look promising.

HIV has three crucial enzymes not found in human cells. The 3-dimensional structure of HIV integrase (which permits the virus to insert part of its genetic information into the cell genes) has been defined. It may be possible to develop a drug to block this enzyme so as to not affect cellular enzymes. AZT targets reverse transcriptase, and other drugs inhibit protease. A new method makes it easier to determine development of drug resistance using high-density, miniaturized oligonucleotide arrays (15,000 probes) on a glass DNA chip; the chips can resequence to PR and RT genes in a single hybridization reaction to determine mutations in the genes that confer decreased resistance to drugs.

(b) Various other biological drugs or vaccines are under study.

In 1988 the first injections of an AIDS vaccine was given in the USA. As of the end of 1994, it was reported that more than 1,500 volunteers have enrolled in 18 federally sponsored trials involving 13 experimental vaccines. So far, 12 participants in phase 1 and phase 2 trials have developed HIV infections; five of these had received a full course of vaccine. It has not been shown that protection by one strain will cross-confer protection to another HIV strain. Any development of combination vaccines would require that individual components are compatible, and individually reactive and the costs of laboratory development and clinical trials are prohibitive. No phase 3 trials in the USA are reported.

The World Health Organization plans to test in phase 3 trial two vaccines derived from HIV surface protein gp120, produced by Biocine Corp.,(a joint venture of Chiron, Ciba-Geigy and Genentech). It was reported that the company has "evaluated and compared the safety and immunogenicity of two recombinant gp120 antigens derived from HIV-1 SF2 in combination with the adjuvant emulsion MF59/MTP-PE. Trial results show denatured non-glycosylated gp120 (ENV2-3) as well as conformationally intact, glycosylated gp120 are safe and immunogenic in HIV infected subjects. Non-glycosylated gp120 env2-3 may be more effective in inducing proliferative responses when compared to CHO-derived gp120. The immunomodulator MTP-PE enhances proliferative responses to both antigens. Viral load assessment by quantitative RNA PCR and responses to selected V3 peptides (SF2, MN, NAconc.LAI,Z6) were assessed." Observations using a recombinant human antibody to envelope gp 120, indicate that 75% of primary isolates of HIV-1 can be neutralized by the monoclonal antibody, tested at concentrations that could be achieved by passive immunization, and that this approach might be useful in interrupting maternal-fetal transmission.

In the USA, a 3-year study in 3000 subjects is using killed HIV minus surface protein (Immune Response Corp.). HIV is killed with a chemical and radiation and the outer protein coat is peeled off. Previously, a 1 year trial in 103 healthy HIV-infected people at nine USA locations was used to evaluate vaccine effects on HIV-1 DNA and RNA levels in PHMCs, on percent of CD4 cells and on other immunologic parameters. PCR measures of HIV DNA showed that HIV in treated patients increased an average of 14% in comparison to 56% in controls. CD4 cells as a fraction of all T lymphocytes fell by an average 0.164% in comparison to 5.03% in controls. CMI and antibody levels were boosted. No serious side effects were noted. No report on indications of any delay of AIDS symptoms or prolongation of life was given.

A vaccine strategy is being developed which combines pseudovirions as primers and synthetic T-B tandem as boosters, so as to allow induction of a strong neutralizing antibody response as well as a CTL response in experimental animals.

Other approaches include the development of peptide vaccines by selective use of modified epitopes, polyvalent V3 loop peptides corresponding to the PND of prevalent HIV strains coupled to various carrier molecules, retroviral vectors encoding HIV-1 proteins, facilitated DNA inoculation, various idiotype-based vaccine strategies, and development of various mucosal vaccines using live, recombinant polio virus and salmonella, microspheres and adjuvants.

Some general observations are useful. It was reported that when HIV inserted genetic material into a cell's DNA, it apparently switched on a nearby cancer-causing gene, inducing a non-B cell lymphoma, and investigators found four lymphoma cases showing HIV insertion in the same spot. They stated that "this causes a lot of concern over the use of retroviruses for anything, for vaccines or even gene therapy. Hooking up a gene to a retrovirus and then infecting human cells might risk cancer." It was reported that a vaccine made from attenuated SIV which had been shown to be safe in adult monkeys, can cause AIDS in newborns. Additional testing of attenuated vaccines with deletions of one or more HIV genes, continues as a result of observations of a long-term healthy individual infected with HIV who lacked a section of the nef gene.

3. TUR AND NVA/EPV

In October 1994, we submitted an abstract for peer review and presentation on Apr. 25, 1995 at the Eighth International Conference on Antiviral Research. We also submitted an abstract on Nov. 28, 1994 for peer review and it was published in Proceedings of American Association of Cancer Organization, March 1995. In 1989, we were asked to and did develop this treatment for AIDS. In view of the long-term results, we decided to share our findings at an international meeting. The above brief review contains data mainly not available in 1989, but useful in substantiating our considerations and deductions at that time. We reasoned that this type of virus keeps surging, changing and is difficult to block. In the 1950's our studies of hundreds of drugs in different chemical categories had resulted in our understanding of virustatic, virucidal effects and we were the first to describe the way in which viral resistance could emerge during the in vivo usage of effective or partially effective purine and pyrimidine analogues. We predicted that this would happen for AZT and like compounds. We reasoned that AIDS would respond to specific active immunotherapy designed to induce a long-lasting cell-mediated immunity only if we were able to find a drug specific for the virus and effective for a long enough period, without inducing resistance, to allow time for a vaccine to work. We reviewed our previous work, made tests and identified a drug (TUR) which proved to be more virus-specific than those reported. We had shown that TUR was a drug which did not appear to induce resistance in diseased animals. In view of the vulnerability and disease conditions of AIDS patients, we studied, compared and selected an effective but also safe and less invasive method of oral delivery of the drug. After studying many case histories, we deduced that the disease was at least partly a cellular disease. Based upon our long studies and harvesting of wild-type as compared with standard viral strains, we had demonstrated in early harvests of infected cells a sharing of epitopes or short sequences with other virus subtypes. As a result of these analyses of the harvests of early proteins induced by viral infection but not a part of the mature virus (non-virion), we felt that we might be able to find gene protein products induced in the cell by the HIV virus which shared properties. The next step was to test individual polypeptides for their ability to induce delayed hypersensitivity reactions and to isolate each early polypeptide with strong antigenic capabilities in inducing cell-mediated immunity. Having identified these, we decided upon a vaccine (EPV-early polypeptide vaccine) but realized the great expense in a small lab of making highly pure vaccine. We then did comparative testing with a slightly less purified mixture (NVA), and reasoned that perhaps these few low molecular weight, noneffective but noninhibitory cell polypeptides might be useful. We reserve the thought, until more patients are studied, that adding a type 1 cytokine product to augment this effect may be needed in rare cases. Because of the possibility that cytokines might augment HIV production, we ruled this out for our initial and phase I studies. In treating Karposi's sarcoma, an additional NVA for a second virus type may be needed.

Herein, we file for a patent on the usage, design and effective procedure for utilizing this combination immunochemotherapy approach, which consists of an AIDS vaccine composed of separated and concentrated early virus-induced or augmented nonvirion polypeptides which induce cell-mediated immunity administered at the peak of effects by a synergistic antiviral drug, thiophenoylurea, which causes minimal or no resistance.

SUMMARY OF THE INVENTION

TUR:

In prior studies, we reported that several purine and pyrimidine analogues and sulfur-containing compounds affect certain host cells in such a way as to inhibit or prevent virus entry or multiplication, some by competitive inhibition. Of these compounds, four showed safety in animals and gave protection in mice infected with poliovirus or influenza virus, but a later development of resistance to each of the three nucleic acid base analogues was demonstrated. Resistance was not seen for the fourth compound, thiophenoyl urea (TUR), which had shown both a reliable inhibitory index in infected cell cultures and a reliable chemotherapeutic and chemoprophylactic index in infected animals. TUR was shown to act by interference with the synthesis of virus by the infected tissue. For our current studies, the top 20 compounds from these previous studies, including TUR, were tested against HIV in vitro. TUR showed a good inhibitory ratio. TUR was administered orally to two late stage cancer patients. TUR was mixed as a 0.03 to 0.04% solution with ten grams of semi-liquid diet food (SLD); the solution was then further mixed in additional SLD up to a total of 300 grams, refrigerated and administered in 100 gram portions, well-mixed, three times daily. This regimen was repeated daily for three weeks, with no measurable side effects.

NVA:

Using methods tested for other diseases early nonstructural HIV components or HIV-induced cellular components were extracted using the separated cell & nuclear membranes from HIV infected cells, and it was determined that these components should be harvested four hrs after infection and stored less than one week at −75 degrees Centigrade (We discovered previously that early viral or virus-induced components which do not become a part of the structure of the mature virus may disappear if frozen too long). Membranes were gently sonicated over ice in neutral phosphate buffered saline, centrifuged and the supernate separated by Sephadex G-200, and second half of second peak eluates, which contained nonvirion antigens (NVA) were concentrated. In a specific lymphocyte (from HIV patient) stimulation assay, a titration effect was observed for each of two polypeptides (after further testing, these were named early polypeptide vaccine, EPV) when individual components of further separated NVA were tested. Remixing with other inactive bands in the NVA did not interfere with activity. Emulsification of 150 mcg protein/0.1 ml NVA with 0.1 ml incomplete Freund's adjuvant was used as vaccine, and was slowly administered intradermally once per month for three months to an HIV positive patient. Cell-mediated immune responses but no toxicity reactions were observed during the course of six months after the first immunization. At six months the patient became HIV seronegative.

CI:

Two AIDS patients received chemoimmunotherapy (CI) consisting of TUR for three weeks, followed by NVA vaccine once per month for three months. Both were still sick at three months, with no sign of improvement. At six months, one patient showed a vast improvement and the other patient (did not improve until about nine months. Both are alive and free of disease five years post-CI, suggesting the feasibility of Phase I clinical studies.

We have invented the usage, design and effective procedure for utilizing anti-HIV TUR (or related chemotherapeutics) as well as for utilizing NVA (or EPV or related or derivative) immunotherapy in the treatment of AIDS and possibly other retroviral diseases. We have invented the combination of TUR and NVA (or similar elements) as a combination immunochemotherapy approach, which consists of an AIDS vaccine (NVA) composed of separated and concentrated early virus-induced or augmented nonvirion polypeptides which induce cell-mediated immunity administered at the height of effects by a synergistic antiviral drug, TUR, which causes minimal or no resistance.

DETAILED DESCRIPTION OF THE INVENTION

The development of an effective drug and vaccine for a synergistic, two-pronged attack on AIDS, involves selection of methods with a knowledge of chemical and physical effects on biological properties as well as humoral and cell-mediated immune mechanisms and coordination of sequence, dosage and route of administration. As described below, first, TUR was tested alone. Second, NVA was tested alone. Third, the chemical drug (TUR) and the biological drug or vaccine (NVA) were used in combination chemoimmunotherapy (CI) in two late stage AIDS patients with favorable results in preparation for a phase I trial of this approach.

TUR:

Several purine and pyrimidine analogues and sulfur-containing compounds affect certain host cells in such a way as to inhibit or prevent virus entry or multiplication, some by competitive inhibition. Of these compounds, four showed safety in animals and gave protection in mice infected with poliovirus or influenza virus, but a later development of resistance to each of the three nucleic acid base analogues was demonstrated [1. Hollinshead, Ariel C. Ph.D. Thesis: A Study of the Effects Produced by Purines and Related Compounds on Virus Propagation. The George Washington University Library, Washington, D. C. Volume 4620, Archival Copy Code # AS36G3, October 1957; 2. Hollinshead, Ariel C. and Smith, Paul K. Relative effectiveness of certain inhibitory chemicals on three types of poliomyelitis virus. J. Pharmacol. Exper. Therapeutics 117: 97–100 (1956); 3. Hollinshead, Ariel C. and Smith, Paul K. Inhibition of poliomyelitis virus by metabolic analogues in mammalian tissue cultures, Federation Proceedings 15: 439 (1956); 4. Hollinshead, Ariel C. and Smith, Paul K. Effect of certain sulfur-containing compounds on the multiplication of poliomyelitis virus in tissue culture. *Antibiotics Annual*, pp. 927–935 (1956); 5. Hollinshead, Ariel C. and Smith, Paul K. Effects of certain purines and related compounds on virus propagation. J. Pharmacol. Exper. Therapeutics 123: 54–62 (1958)]. The fourth compound, thiophenoyl urea (TUR) was selected since no resistance had been demonstrated and at effective dosage, toxicity was not evident [TUR was originally obtained in 1954 as Miles Ames No.261, Dr. Hollinshead visited and shared early results with Dr. Desmond O'Sullivan at Courtauld Institute of Biochemistry, who was kind enough to prepare this and similar compounds for Dr. Hollinshead. Lot comparisons were reliable and permitted re-evaluations in vitro and in vivo. Methods of making the drugs were published by D. G. O'Sullivan and A. K. Wallis in article entitled Synthesis and H NMR Spectra of Thiophenoyl-, Furoyl- and Pyrroylureas with Antiviral Properties, Z. Naturforsch.B: Anorg. Chem., Org. Chem. Vol. 30B (7–8, 600–602, 1975; Chem. Abstr. 83: 526 (1975p9 . In comparative tests, performed double blind and in triplicate, of twenty compounds including TUR against HIV-1 in vitro, TUR showed a good inhibitory ratio of greater than 8 (1.0 mg/ml down to less than 0.12 mg/ml) with activity apparent at low dosage in infected cells. It was determined that TUR acts by interference with the synthesis of virus by the infected cells. Previously, our studies of chemotherapy and chemoprophylaxis of poliovirus in mice indicated that TUR could possibly be of use in preventing carrier states or in stopping further development of disease in a community exposed to possible infection. TUR may be prepared as 0.03 to 0.04% (30 or 40 mg) per ten grams of semi-liquid diet food (SLD) solution, well-mixed, given by spoon or dropper in three parts daily, or, preferrably the solution is then further diluted in SLD up to a total of 300 grams, refrigerated and administered in 100 gram portions, well-mixed, three times daily. TUR was administered orally to two late stage cancer patients, in the preferred preparation, TID for three weeks, with no measurable side effects.

NVA:

Using newly applied methods and a few of the methods tested for other diseases [6. Hollinshead, A. C., McCammon, J. R. and Yohn, D.,Immunogenicity of a soluble transplantation antigen from adenovirus 12-induced tumor cells demonstrated in inbred hamsters (PD-4), Canadian J. Microbiol. 18: 1365–1369 (1972); 7. Hollinshead, A. C., Lee, O. B., Chretien, P., Tarpley, J., Rawls, W. and Adam, E., Antibodies to herpesvirus nonvirion antigens in squamous carcinomas. Science 182: 713–715 (1973); 8. Hollinshead, A., Stewart, T. H. M., Takita, H., Dalbow , M. and Concannon, J., Adjuvant TAA specific active immunotherapy trials. Tumor-associated antigens, Cancer 60: 1249–62 (1987); 9. Hollinshead, Ariel, Takita, Hiroshi, Stewart, Thomas and Raman, S, Specific Active Immunotherapy. Immune Correlates of Clinical Responses and an Update of Immunotherapy Trials Evaluations, Cancer 62: 1662–1671 (1988); Hollinshead, Ariel C., Inventor: Methods of Preparing Epitopes of Tumor Associated Antigens. U.S. Pat. No. 4,890,781 , Mar. 7, 1989, early nonstructural HIV components were extracted using the separated cell and nuclear membranes from HIV infected cells harvested four hrs after infection and stored less than one week at −75 degrees Centigrade (We discovered previously that early viral components which do not become a part of the structure of the mature virus may disappear if frozen too long). Although appropriate cloned cell lines may be used, we chose to use a known method whereby autologous peripheral blood lymphocytes are separated by Ficoll-Hypaque gradient centrifugation, re-suspended in RPMI-1640, counted, washed until 90% viability, and re-suspended in a final concentration of 1.8×10 million cells/ml in RPMI-1640 containing 15%, and for the last two days of culture 0%, fetal calf serum, penicillin and streptomycin. To determine % viability and required number of washings, three cell aliquots are counted using white cell diluent, trypan blue and neutral red, respectively. Sterility monitoring is conducted throughout the procedure. Cells are then cultured at approximately 1000 cells per ml of RPMI medium, incubated for 3–4 days in 5% $CO_2$ humidified 37 degree Centigrade incubator and infected with HIV, harvested at four hours and washed and membranes extracted using a previously described modified Davies procedure which consists of a rapid stepwise technique, to minimize degradative enzymatic activity, with suspensions of isotonic to hypotonic saline solutions. The suspension of membrane material is then subjected to sequential low frequency (9 kc/sec) sonication over ice in neutral phosphate buffered saline. More rigorous sonication tends to produce detrimental thermal effects, solubilization of unwanted materials, increased risks of protein degradation and loss of antigenic activity. The suspension, soluble membrane sonicate, is centrifuged and the supernate separated over an already prepared Sephadex G-200 column in the cold room collected in test tubes,with small samples removed and concentrated for a comparison of gel electrophoresis patterns of standards, uninfected cells similarly treated and infected cells containing mature virions. Aliquots of differing patterns were concentrated by ultrafiltration, diluted 100× and reconcentrated for pretesting of cell-mediated immunoreactivity using standard specific lymphocyte (from HIV patient) stimulation assays (SLS). It was established that the preferred method of preparation was the selection of the last half of the second peak eluates, since this region contained active virus-induced cellular or non-virion antigens(NVA). Additional studies include the following: The remaining separated material from the last half of the second peak was pooled and also concentrated by Amicon ultrafiltration to a uniform 150 mcg protein/0.1 ml per aliquot, and labeled as NVA. Bands separated from three NVA aliquots by electrophoresis were further separated, a portion of each band further analyzed by 2D-immunoelectrophoresis, and the rest each eluted and concentrated. In an SLS assay, a titration effect was observed for each of two bands (later named early polypeptide vaccine, EPV). Remixing of EPV with the inactive bands in the NVA did not interfere with SLS activity.

We then conducted GLP tests of NVA, including tests in rabbit and guinea pigs were conducted with good results. Three AIDS patients were skin-tested for anergy using mumps and/or streptokinase-streptodornase and recording delayed hypersensitivity responses. 5 mcg and 50 mcg NVA tested DHR positive in a nonanergic patient. Emulsification of 150 mcg protein/0.1 ml NVA with 0.1 ml incomplete Freund's adjuvant was used as vaccine, administered slowly intradermally once per month for three months to an HIV positive patient. Cell-mediated immune responses but no toxicity reactions were observed during the course of six months after the first immunization. At six months the patient became HIV seronegative.

CHEMOIMMUNOTHERAPY:

Two AIDS patients received TUR for three weeks, followed by NVA vaccine once per month for three months. Both were still sick at three months, with no sign of improvement. At six months, one patient showed a vast improvement and the other patient did not improve until about nine months. Lung, liver and nodal lesions cleared gradually, viral antibody fell to low levels [confirmed by an improved test of frozen specimens at a later date using a bDNA assay (10. Nucleic Acid Research Sympos. Series 24: 197–200, 1991)], possibly a dormant state [11.Hollinshead, A. , Soluble tumor antigens used in clinical trials of immunotherapy, Chapter, pages 281–313, In: *Cellular Immune Mechanisms and Tumor Dormancy*, Ed. Thomas H. M. Stewart, Publishers CRC Press, Inc., workshop held at Ottawa Univ. Med. Ctr. on Oct 1–2, 1991, book published 1992 by CRC Press Inc., Corporate Blvd., N.W., Boca Raton, Fla., 33431 USA] and CD4/CD8 ratios normalized. Both are alive and free of disease more than five years post-CI, suggesting the feasibility of phase I clinical studies.

In early considerations, we felt that the evidence suggested that cellular elements play a strategic role in the development of AIDS. Even if all enzymes were clinically targeted, and even if parts of or all of the various HIVs were targeted, HIV apppeared to be a wily, difficult virus to eradicate, with a high level of mutation, configurational change, target differentiation, diversity of entry pathways and escape mechanisms and, therefore the ability to avoid chemical or biologic drug interventions. Some six years ago we designed this combination treatment based in part on recognition of early virus-induced protein changes in the cell. Current theory holds that a strong cellular immune response with a type I cytokine profile is the best protector against HIV. Once HIV and other influences gain a foothold, usage of cytokines alone would be precluded; however, any therapeutic design should include measurement, monitoring and perhaps, in future when indicated safe by other investigators, it may be useful to include usage of such agents to insure this response. As described in the background section, a second viral NVA may be needed for Karposi's sarcoma. Our long experience in the development of cancer vaccines which induce long-lasting cell-mediated immunity and our experiences in studies of early nonvirion or virus-induced cellular components for several other viruses, aided in the development of an AIDS vaccine.

Based on our recent studies, we realized the importance of combination immunochemotherapy in the treatment of an already developed disease like AIDS. Also, based on our earlier studies and our understanding of a virus with properties like HIV, we understood the significance of developing chemotherapy which blocks early virus-induced or -augmented processes and does not cause later resistance. Such chemotherapy would need to address the surges of viral replication after recovery from initial therapy, and would need to act both on the humoral and cellular immune responses in such a way as to lower the viral load and begin to alter abnormal T cell subset and other cell responses, in order to pave the way for effective vaccine immunization timed for administration at the peak of the drug effects. Recently, at the same conference where we first presented our findings, we learned in vitro studies indicate that the functional groups of certain sulfur- containing compounds, especially thiophenes, are likely to attack the thiolates that chelate the zinc fingers of the p7 nucleocapsid protein of HIV1 [12. W. G. Rice, C. A. Schaeffer, J. A. Turpin, L. Coren, R. C. Sowder II, B. Kane, J. Bader, L. O. Arthur and L. E. Henderson, New Classes of Reagents that Attack Conserved and Chemically Reactive Zinc Fingers in Retroviral Nucleocapsid Proteins: A strategy for Rational Drug Design, Proc. Eight Internatl. Conf. Antiviral Res., Abstr. 18, p.A235 (1995)]. This may explain in part the manner in which TUR appears specifically to prevent or slow virus production in the infected AIDS patient in order to permit NVA to take effect. In our previous studies (1–5, above), we reported several antiviral thiophene, sulfone, phenoxathiin and simple aliphatic sulfur-containing compounds with varying degrees of activity. Our studies of those drugs which were active showed that thiophene derivatives caused a marked delay of virus appearance, sulfones seemed to affect the host cell itself, and phenoxathiin and phenothiazine derivatives were virucidal, as well as all but one of the aliphatic compounds. We showed that the virustatic activity of some of the thiophene compounds could be reversed; four were competitively reversed, namely 3-thiophenecarboxylic acid by cysteine, 2-thiophenealanine by phenylalanine, ethanol-2 methyl mercapto by ethanolamine and thiophenoyl urea (TUR) by methionine. The development [13.Hollinshead, A. , Chemo-immunotherapy (CI) by Thiophenoyl Urea (TUR) & Nonvirion antigen vaccine (NVA) for AIDS patients, (abstract submitted 14 Oct.1994), published in Proc. Eighth International Conference on Antiviral Research, Santa Fe, N. Mex., Abstract no. 116 p.A286 (presented Tuesday, 25 Apr. 1995); 14. Hollinshead, A. Developing a new AIDS chemoimmunotherapy (CI), Abstract submitted 28 November 1994, published in. Proc. ASCO 14: Abstr.837, p.292 (1995)]. of a strong antiviral effect coupled with the development of an effective, long-lasting cell-mediated immunity is a useful synergistic combination therapy when using appropriate timing, dosage, means of administration and selected agents which work together.

While the present invention has been described with respect to certain preferred embodiments, it will be apparent that the usage and continued process of clinical and laboratory studies toward which the present application is directed is not to be limited to any such preferred embodiments, but will include such alterations and modifications thereof as will be obvious to those of ordinary skill in the art. As to all such obvious alterations and modifications, I intend that they be included within the purview of my invention, which is to be limited only by the scope, including equivalents, of the following appended claims.

What is claimed is:

1. A method for inhibiting HIV replication in an HIV positive or AIDS patient comprising the step of administering an effective amount of thiophenoyl urea to the patient.

2. A method for inducing anti-HIV/AIDS cell-mediated and humoral immunity in an HIV positive or AIDS patient, comprising the step of administering an effective amount of an HIV non-virion antigen vaccine to the patient the HIV non-virion antigen vaccine consisting essentially of early nonstructural HIV components and HIV-induced cellular components which do not become part of the mature virus.

3. The method of claim 1, wherein the thiophenoyl urea is administered orally.

4. The method of claim 3, wherein the thiophenoyl urea is mixed as 0.03 to 0.04% solution in 10 grams of a semi-liquid diet food (SLD), said mixture be further mixed with additional SLD to 300 grams, refrigerated, and administered three times daily in well-mixed 100 gram amounts and repeated daily for three weeks.

5. The method of claim 2 wherein, the non-virion antigen vaccine is in form of an emulsion containing 150 microgram nonvirion antigen protein in 0.1 ml emulsified with 0.1 ml of incomplete Freund's adjuvant, administered slowly intradermally once per month for three months.

6. A method for normalizing CD4/CD8 ratio in an HIV positive or AIDS patient comprising the step of administering an effective amount of thiophenoyl urea in combination with an HIV non-virion antigen vaccine to the patient, the HIV non-virion antigen vaccine consisting essentially of early nonstructural HIV components and HIV-induced cellular components which do not become part of the mature virus.

7. The method of claim 6, wherein the thiophenoyl urea is administered prior to the HIV non-virion antigen vaccine by mixing the thiophenoyl urea as 0.03 to 0.04% solution in 10 grams of a semi-liquid diet food (SLD), said mixture be further mixed with additional SLD to 300 grams, refrigerated, and administered three times daily in well-mixed 100 gram amounts and repeated daily for three weeks followed by administration of HIV non-virion antigen vaccine wherein the HIV non-virion antigen is in form of an emulsion containing 150 microgram nonvirion antigen protein in 0.1 ml emulsified with 0.1 ml of incomplete Freund's adjuvant, administered slowly intradermally once per month for three months.

8. A method for inhibiting HIV replication and inducing anti-HIV/AIDS cell-mediated and humoral immunity in an HIV positive or AIDS patient, comprising the step of administering an effective amount of thiophenoyl urea in combination with an HIV non-virion antigen vaccine to the patient, the HIV non-virion antigen vaccine consisting essentially of early nonstructural HIV components and HIV-induced cellular components which do not become part of the mature virus.

9. The method of claim 8, wherein the thiophenoyl urea is administered prior to the HIV non-virion antigen vaccine by mixing the thiophenoyl urea as 0.03 to 0.04% solution in 10 grams of a semi-liquid diet food (SLD), said mixture be further mixed with additional SLD to 300 grams, refrigerated, and administered three times daily in well-mixed 100 gram amounts and repeated daily for three weeks followed by administration of HIV non-virion antigen vaccine wherein the HIV non-virion antigen is in form of an emulsion containing 150 microgram nonvirion antigen protein in 0.1 ml emulsified with 0.1 ml of incomplete Freund's adjuvant, administered slowly intradermally once per month for three months.

* * * * *